US012673169B2

(12) United States Patent
Cong et al.

(10) Patent No.: US 12,673,169 B2
(45) Date of Patent: Jul. 7, 2026

(54) SYRINGE AND NEEDLE HUB HAVING PROTECTIVE COVER

(71) Applicant: SHANDONG WEIGAO GROUP MEDICAL POLYMER CO., LTD., Weihai (CN)

(72) Inventors: Rinan Cong, Weihai (CN); Shuai Chen, Weihai (CN); Xiaobing Li, Weihai (CN); Jianjun Yu, Weihai (CN)

(73) Assignee: SHANDONG WEIGAO GROUP MEDICAL POLYMER CO., LTD., Weihai (CN)

( * ) Notice: Subject to any disclaimer, the term of this patent is extended or adjusted under 35 U.S.C. 154(b) by 463 days.

(21) Appl. No.: 18/559,070

(22) PCT Filed: Jun. 15, 2021

(86) PCT No.: PCT/CN2021/100068
§ 371 (c)(1),
(2) Date: Nov. 6, 2023

(87) PCT Pub. No.: WO2022/233081
PCT Pub. Date: Nov. 10, 2022

(65) Prior Publication Data
US 2024/0238535 A1 Jul. 18, 2024

(30) Foreign Application Priority Data

May 6, 2021 (CN) .......................... 202110490075.2
May 6, 2021 (CN) .......................... 202120963124.5

(51) Int. Cl.
*A61M 5/32* (2006.01)
(52) U.S. Cl.
CPC ................................ *A61M 5/3257* (2013.01)
(58) Field of Classification Search
CPC .................................................. A61M 5/3257
See application file for complete search history.

(56) References Cited

U.S. PATENT DOCUMENTS

2002/0193744 A1 12/2002 Alesi et al.
2003/0060773 A1 3/2003 Nguyen
(Continued)

FOREIGN PATENT DOCUMENTS

CN 202724380 U 2/2013
CN 103520807 A 1/2014
(Continued)

OTHER PUBLICATIONS

The 2nd Office Action dated Feb. 17, 2025 for the Chinese Patent Application No. CN202110490075.2. English Translation of the 1st Office Action Provided by http://globaldossier.uspto.gov.
(Continued)

*Primary Examiner* — Dung T Ulsh
(74) *Attorney, Agent, or Firm* — Yue (Robert) Xu; Apex Attorneys at Law, LLP

(57) ABSTRACT

Disclosed are a syringe and a needle hub having a protective cover. The needle hub having a protective cover includes a needle hub body and a protective cover that are integrally formed by means of injection molding. The needle hub body is used for inserting and fixing a needle tube. The protective cover is used for flipping at an angle at which the opening faces the needle hub body and the needle tube, and covering the needle hub body and the needle tube. The root of the protective cover is locked to the peripheral side of the needle hub body when the protective cover is flipped and covers the needle hub body.

7 Claims, 4 Drawing Sheets

(56)                    References Cited

U.S. PATENT DOCUMENTS

| | | | | |
|---|---|---|---|---|
| 2005/0065482 | A1 | 3/2005 | Hauri et al. | |
| 2015/0165133 | A1 | 6/2015 | Zhang et al. | |
| 2016/0158458 | A1 | 6/2016 | Feng et al. | |
| 2017/0258990 | A1* | 9/2017 | Wei ..................... | A61M 5/3216 |
| 2019/0343439 | A1 | 11/2019 | Wang | |
| 2021/0260304 | A1* | 8/2021 | Ryan ................... | A61M 5/3216 |

FOREIGN PATENT DOCUMENTS

| | | | | |
|---|---|---|---|---|
| CN | 203694278 | U | 7/2014 | |
| CN | 204910354 | U | 12/2015 | |
| CN | 205287134 | U | 6/2016 | |
| CN | 106730172 | A | 5/2017 | |
| CN | 107737391 | A | 2/2018 | |
| CN | 211749645 | U | 10/2020 | |
| CN | 217828540 | U | 11/2022 | |
| WO | WO-2020241708 | A1 * | 12/2020 | .......... A61M 5/3216 |

OTHER PUBLICATIONS

The 1st Office Action dated Oct. 25, 2024 for the Chinese Patent Application No. CN202110490075.2. English Translation of the 1st Office Action Provided by http://globaldossier.uspto.gov.
International Search Report for PCT/CN2021/100068 mailed Feb. 9, 2022, ISA/CN.

* cited by examiner

SYRINGE AND NEEDLE HUB HAVING PROTECTIVE COVER

The present application is the national phase of international patent application No. PCT/CN2021/100068, titled "SYRINGE AND NEEDLE HUB HAVING PROTECTIVE COVER", filed on Jun. 15, 2021 which claims the priority to Chinese Patent Application No. 202110490075.2, titled "SYRINGE AND NEEDLE HUB HAVING PROTECTIVE COVER", filed with the China National Intellectual Property Administration on May 6, 2021, and to Chinese Patent Application No. 202120963124.5, titled "SYRINGE AND NEEDLE HUB HAVING PROTECTIVE COVER", filed with the China National Intellectual Property Administration on May 6, 2021, all of which are incorporated herein by reference in their entireties.

FIELD

The present application relates to the technical field of needle assemblies, and in particular to a needle hub having a protective cover. The present application further relates to a syringe including the needle hub having a protective cover.

BACKGROUND

For syringes, used needles are possible to accidentally stick the human body, which in turn can cause disease infection, and thus there is a need to shield the used needles.

The vast majority of syringes typically utilize a self-contained needle sheath to shield the needle.

Since the self-contained needle sheath of the syringe requires two hands to operate, and medical personnel are often unable to keep their hands free during medical operations, a syringe with an anti-needle-stick protective sheath is presently available. This syringe with an anti-needle stick protective sheath allows the medical personnel to operate the protective sheath with one hand after the injection is completed, so that the protective sheath shields the needle.

However, the conventional syringe with an anti-needle-stick protective sheath not only has a complex structure, is difficult to manufacture and process, and is inefficient, but also has higher requirements for medical personnel to operate the protective sheath in order to make the protective sheath accurately and safely shield the needle when it is used. In other words, the medical personnel are susceptible to improper shielding of the needle when operating, which poses a greater safety risk.

SUMMARY

It is an object of the present application to provide a needle hub having a protective cover, which can simplify the manufacturing and processing, reduce the cost, and also simplify a shielding operation of the protective cover on a needle, and improve the safety and reliability of use. Another object of the present application is to provide a syringe including the needle hub having a protective cover.

To realize the above objects, a needle hub having a protective cover is provided according to the present application. The needle hub includes a needle hub body and a protective cover which are integrally formed by injection molding. The needle hub body is configured for insertion and fixation of a needle. The protective cover is configured to be turned over with an opening thereof facing towards the needle hub body and the needle to cover the needle hub body and the needle. A root portion of the protective cover is locked to a periphery of the needle hub body when the protective cover is turned over and covers the needle hub body.

In an embodiment, a positioning post is provided on the periphery of the needle hub body; and the protective cover is provided with a positioning hole configured for insertion and positioning of the positioning post.

In an embodiment, the number of the positioning post is two, and the two positioning posts are located on two opposite sides of the needle hub body, respectively; two positioning holes arranged oppositely are provided on a root side wall of the protective cover; and a spacing between the two positioning holes is less than a maximum spacing between the two positioning posts.

In an embodiment, the root side wall is further provided with a guiding sliding slot; and a bottom surface of the guiding sliding slot smoothly transitions from an edge of the root side wall to an inner bore rim of the positioning hole.

In an embodiment, reinforcing ribs are provided in a cavity of the protective cover; and a demolding direction of the reinforcing ribs is the same as a direction of the lateral opening of the protective cover.

In an embodiment, the protective cover includes a first curved side wall; the first curved side wall is located at an opposite side of the lateral opening of the protective cover; and a finger recess is provided between a root portion and a head portion of the first curved side wall.

In an embodiment, the root portion is smoothly bulged, relative to the head portion, to form the finger recess.

In an embodiment, a plastic joint portion, which is integrally injection molded with the needle hub body and the protective cover, is provided between the needle hub body and the protective cover; a slender notched groove is formed on a surface of the plastic joint portion; and the protective cover is turned over around a center axis of the notched groove and covers the needle hub body and the needle.

In an embodiment, the notched groove has a trapezoidal cross-section; and a groove width of the notched groove tapers inwardly from the surface of the plastic joint portion.

A syringe, including the needle hub having a protective cover, is further provided according to the present application.

Compared with the above conventional technology, the needle hub with a protective cover according to the present application includes the needle hub body and the protective cover which are integrally formed by injection molding.

In the needle hub having a protective cover, the needle hub body is configured for insertion and fixation of the needle, and the protective cover is configured to be turned over with the opening thereof facing towards the needle hub body and the needle to cover the needle hub body and the needle. The protective cover is turned over with its own root portion, which is a portion connected to the needle hub body, as a joint, and the root portion of the protective cover is interlocked with the periphery of the needle hub body when it covers the needle hub body, so as to realize the relative fixation of the protective cover and the needle hub body and the needle in the current position.

For the needle hub with a protective cover according to the present application, the protective cover and the needle hub body are injection molded to form a single part, which can not only simplify the assembly process and the assembly difficulty during the product assembly process, thereby saving cost and improving production efficiency, but also fundamentally avoid the separation, relative movement or rotation of the protective cover and the needle hub body with the needle being inserted in the process of using the product, and thus avoid the misalignment of the protective cover with the needle, or the detachment of the protective cover from the needle in the covering state, during the process of turning over and covering, thereby improving the efficiency and safety of the shielding operation.

BRIEF DESCRIPTION OF THE DRAWINGS

In order to more clearly illustrate technical solutions in embodiments of the present application or in the conventional technology, the drawing referred to for describing the embodiments or the conventional technology will be briefly described hereinafter. Apparently, the drawings in the following description illustrate only embodiments of the present application. Other drawings may be obtained by those skilled in the art based on the provided drawings without any creative efforts.

REFERENCE NUMERALS ARE AS FOLLOWS

01—needle, 02—needle barrel, 03—needle sheath, 1—needle hub body, 2—protective cover, 21—first curved side wall, 3—plastic joint portion, 4—positioning post, 5—positioning hole, 6—guiding sliding slot, 7—reinforcing rib, 8—notched groove.

DETAILED DESCRIPTION OF THE EMBODIMENTS

The technical solutions in the embodiments of the present application will be described clearly and completely hereinafter in conjunction with the accompanying drawings in the embodiments of the present application, and it is apparent that the described embodiments are only a part of the embodiments of the present application, rather than all of the embodiments. Based on the embodiments in the present application, all other embodiments obtained by those skilled in the art without creative efforts fall within the scope of protection of the present application.

In order to enable those skilled in the art to better understand the embodiments of the present application, the present application is described in further detail hereinafter in conjunction with the accompanying drawings and specific embodiments.

Figure 1:
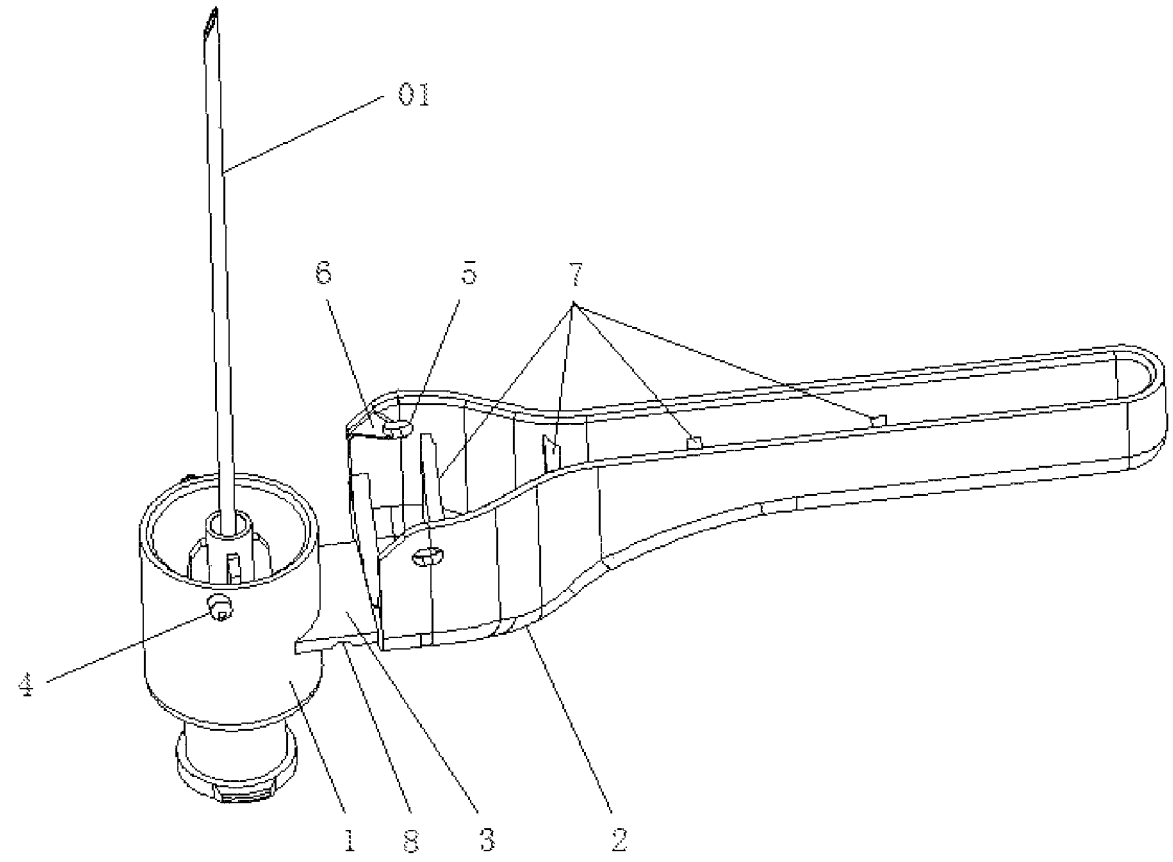
FIG. 1 is a schematic structural view of a needle hub having a protective cover according to an embodiment of the present application.
Figure 2:
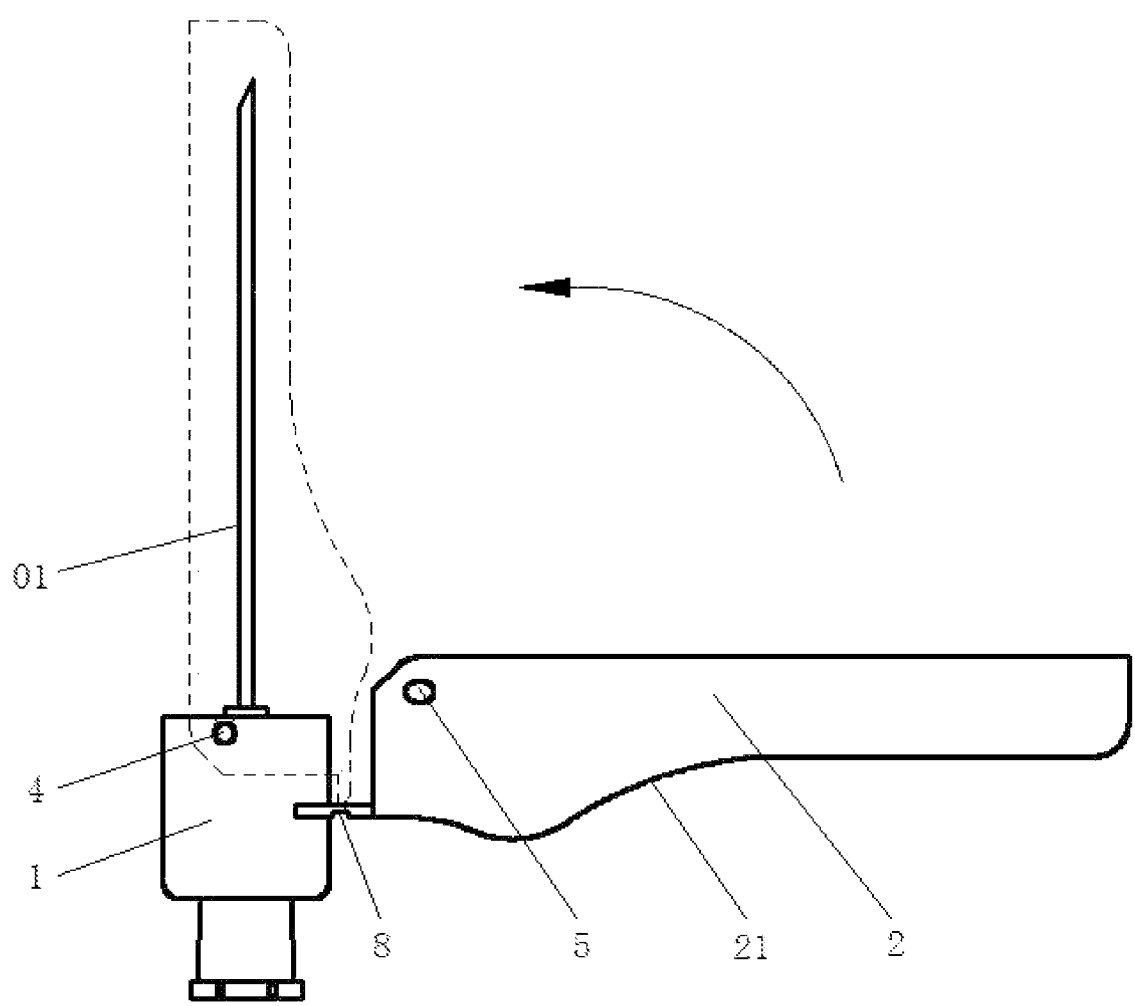
FIG. 2 is a front view of FIG. 1.
Figure 3:
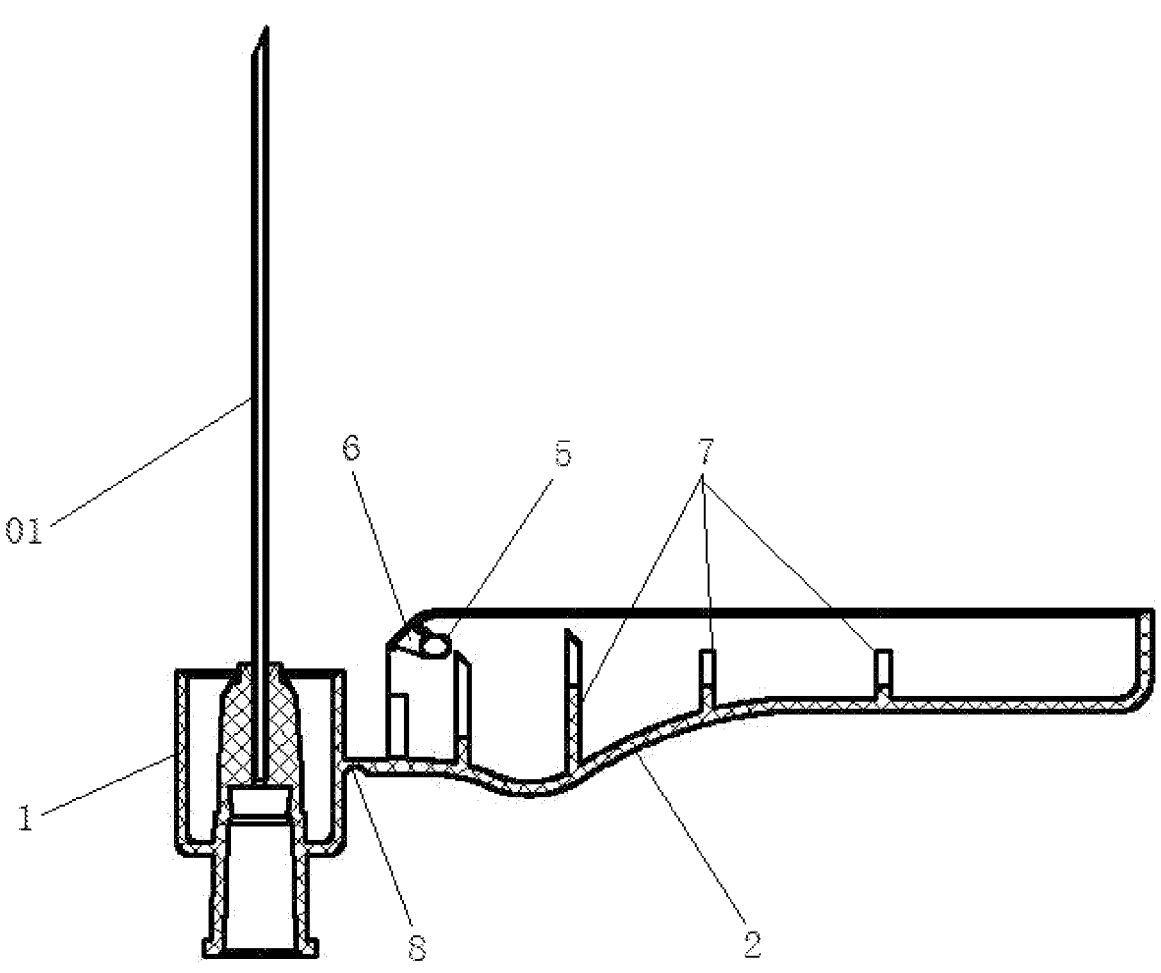
FIG. 3 is a cross-sectional view of a needle hub having a protective cover according to an embodiment of the present application.
Figure 4:
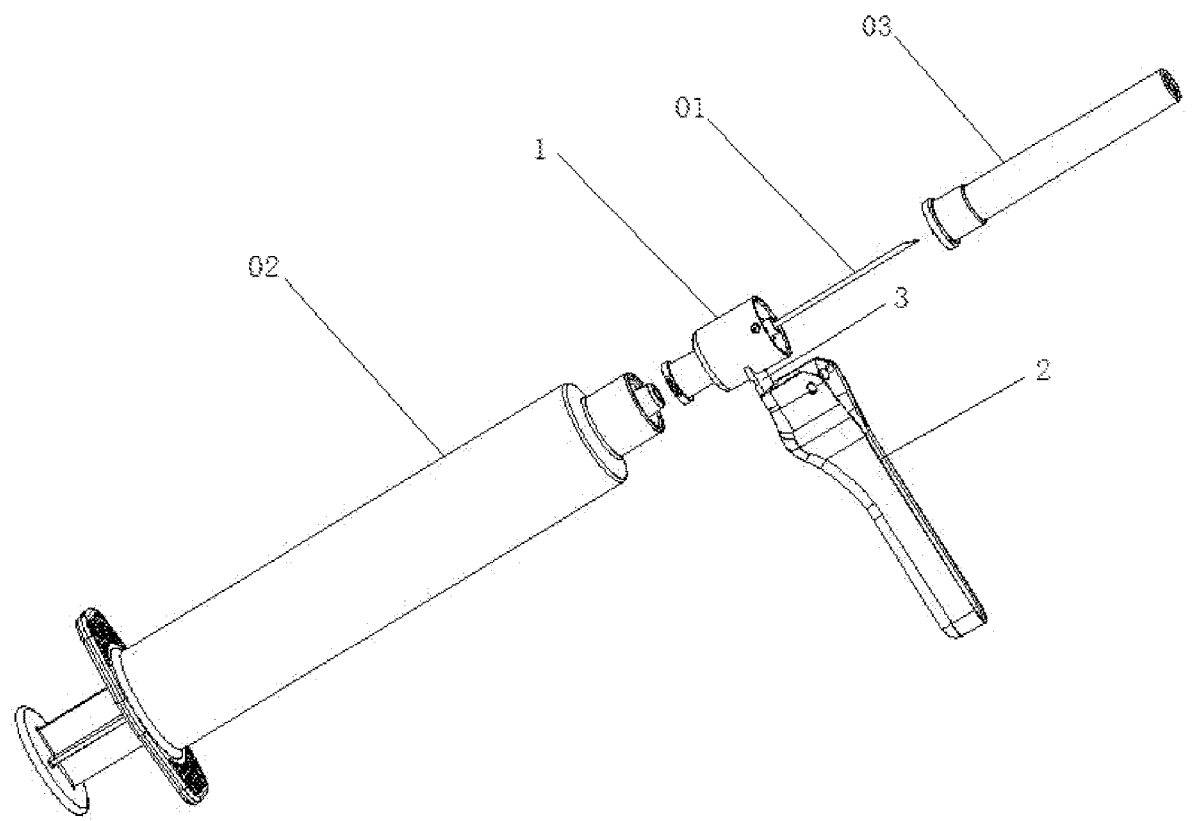
FIG. 4 is a schematic structural view of a syringe according to an embodiment of the present application.

Referring to FIGS. 1 to 4, FIG. 1 is a schematic structural view of a needle hub having a protective cover according to an embodiment of the present application; FIG. 2 is a front view of FIG. 1; FIG. 3 is a cross-sectional view of a needle hub having a protective cover according to an embodiment of the present application; and FIG. 4 is a schematic structural view of a syringe according to an embodiment of the present application.

A needle hub having a protective cover is provided according to the present application. The needle hub includes a needle hub body 1 configured for insertion and fixation of a needle 01, and a protective cover 2 configured for covering the needle hub body 1 and the needle 01. The protective cover 2 is disposed at one side of the needle hub body 1, and the protective cover 2 and the needle hub body 1 are integrally formed by injection molding. During the usage of the needle hub having a protective cover, the protective cover 2 is turned over around its own root portion, which is a portion connected with the needle hub body 1, so that the root portion of the protective cover 2 covers and is locked to a periphery of the needle hub body 1, and a head portion and a middle portion of the protective cover 2 cover the needle 01 inserted in the needle hub body 1.

The root portion of the protective cover 2 being locked to the periphery of the needle hub body 1 means that when the head portion and the middle portion of the protective cover 2 cover the needle 01, the root portion of the protective cover 2 is located at an outer side of the periphery of some or all of the needle hub body 1 and is fixedly connected to the needle hub body 1. The ways for realizing locking between the protective cover 2 and the needle hub body 1 include and are not limited to a mortise-tenon connection therebetween by using a concave-convex structure, the protective cover 2 being interference sleeved outside the needle hub body 1, and the like.

In the present embodiment, the protective cover 2 may be configured as an elongated cover structure with an opening formed on a side, forming an elongated cover shape with a lateral opening. Accordingly, two ends of the protective cover 2 along a lengthwise direction are a head portion and a root portion of the protective cover 2, respectively. The root portion is connected to the needle hub body 1 for covering and connecting to the needle hub body 1. The head portion and the middle portion are configured for covering the needle 01 inserted in the needle hub body 1. Apparently, for the above protective cover 2 in the form of an elongate cover body, the side direction of the protective cover 2 refers to the radial periphery of the protective cover 2, as distinguished from the two ends of the protective cover 2 in the lengthwise direction.

The shape of the needle hub body 1 may be specifically set in combination with the actual need. For example, the needle hub body 1 may be configured as a tubular column structure. With reference to FIGS. 1 to 3, a first cylinder for insertion of the needle 01 is provided in one of the ends of the needle hub body 1 in the axial direction, a cross-shaped reinforced plate is provided at the outer periphery of the first cylinder, and a second cylinder is sleeved outside the first cylinder and the cross-shaped reinforced plate. A Luer taper is provided in the other end of the needle hub body 1 along the axial direction to be mated with a needle barrel 02 of any specification.

For the protective cover 2 and the needle hub body 1 which are integrally formed by injection molding, the protective cover 2 and the needle hub body 1 may be made of materials having elasticity or plasticity, including and not limited to thermoplastic materials, so that the root portion of the protective cover 2 can be deformed to achieve turning over of the protective cover 2.

Since the needle hub having a protective cover is formed by an integral injection molding process, in order to facilitate the demolding, both outer peripheral contours and inner cavities of the needle hub body 1 and the protective cover 2 extend towards the respective demolding direction. Furthermore, cavity openings of both the needle hub body 1 and the protective cover 2 may be distributed in the same direction when the needle hub having a protective cover is not yet in use.

In summary, in the needle hub having a protective cover according to the present application, the protective cover and the needle hub body 1 are injection molded to form a single part, which simplifies the process flow and assembly difficulty of the syringe including the needle hub during the assembly process of the product, and saves the costs and improves the production efficiency. During the use of the product, there is no risk of the protective cover 2 separating from the needle hub body 1 inserted with the needle 01, and no risk of relative movement or rotation between the protective cover 2 and the needle hub body 1, thereby avoiding misalignment of the protective cover 2 with the needle 01 during the process of turning over and covering, or avoiding the protective cover 2 in the covering state from detaching from the needle 01.

The needle hub having a protective cover according to the present application is described further below in conjunction with the accompanying drawings and embodiments.

On the basis of the above embodiments, the needle hub having a protective cover according to the present application utilizes a shaft-hole fitting to lock the root portion of the protective cover 2 to the needle hub body 1.

For example, a positioning post 4 is provided at the periphery of the needle hub body 1, and a positioning hole 5 for insertion and positioning of the positioning post 4 is formed in the protective cover 2. The positioning hole 5 may be formed in a cavity of the protective cover 2 or in a wall of a cover body of the protective cover 2. The positioning post 4 and the positioning hole 5 may be injection molded by using a slider in the mold, which is easy to demold and has a high molding quality.

The manner, in which the positioning post 4 and the positioning hole 5 are connected with each other when the protective cover 2 is turned over to the peripheral side of the needle hub body 1, depends on the relative positional relationship of the positioning post 4 and the positioning hole 5.

For example, in a case that the positioning post 4 and the positioning hole 5 are distributed oppositely, the axial direction of the positioning post 4 and the axial direction of the positioning hole 5 are in a turning over plane of the protective cover 2, then the positioning hole 5 approaches the axial end of the positioning post 4 for insertion when the protective cover 2 is turned over to the needle hub body 1. At this time, the positioning hole 5 and the positioning post 4 may be connected by means of the axial-hole interference fit.

In a case that the axial direction of the positioning hole 5 and the axial direction of the positioning post 4 are both perpendicular to the turning over plane of the protective cover 2, then, when the protective cover 2 is turned over to the needle hub body 1, the protective cover 2 is forced by the needle hub body 1 to deform and expand, so that the positioning hole 5 is fitted to the positioning post 4. Since in this example, the axial direction of the positioning hole 5 and the axial direction of the positioning post 4 are both perpendicular to the turning over plane of the protective cover 2, the positioning hole 5 already fitted to the positioning post 4 is not allowed to automatically detach from the positioning post 4, achieving the fixed connection between the needle hub body 1 and the protective cover 2.

Taking FIG. 1 as an example, the needle hub having a protective cover may be provided with two symmetrically distributed positioning posts 4 on the peripheral side of the needle hub body 1, and correspondingly, two oppositely distributed positioning holes 5 are provided on the root sidewall of the protective cover 2, and a spacing between the two positioning holes 5 is less than a maximum spacing between the two positioning posts 4.

The maximum spacing between the two positioning posts 4 refers to a distance between two axial ends, which are furthest apart, of the two positioning posts 4.

In the needle hub having a protective cover, when the protective cover 2 is turned over towards the needle hub body 1 and the needle 01, the root side wall of the protective cover 2 is forced by the needle hub body 1 to expand, so that the spacing between the two positioning holes 5 expands to a spacing not less than the maximum spacing between the two positioning posts 4, allowing the positioning holes 5 to be fitted to the positioning posts 4. Once the positioning holes 5 are fitted to the positioning posts 4, the protective cover 2 and the needle hub body 1 are locked in a current position. Unless a large external force is applied to the protective cover 2 and the needle hub body 1, the protective cover 2 is not easily detached from the needle hub body 1 again.

In order to achieve a better technical effect, on the basis of the above embodiments, the root side wall of the protective cover 2 according to the present application is further provided with a guiding sliding slot 6.

The guiding sliding slot 6 and the positioning holes 5 are provided in the same face-like structure, i.e. in the same root side wall. A bottom surface of the guiding sliding slot 6 smoothly transitions from an edge of the root side wall to an inner bore rim of the positioning hole 5, and the width of the guiding sliding slot 6 tapers from the edge of the root side wall to the inner bore rim of the positioning hole 5.

In conjunction with FIG. 1, if the surface of the root side wall on which the guiding sliding slot 6 is located is taken as a reference, the bottom surface of the guiding sliding slot 6 may be parallel to the surface of the root side wall as described before, or may be configured as a sloping surface inclined relative to the surface as described before.

The bottom surface of the guiding sliding slot 6 being configured as an inclined surface is described as an example. For the two oppositely distributed root side walls of the protective cover 2, the spacing between the bottom surfaces of the two guiding sliding slots 6 located at the two root side walls, respectively, is not constantly equal. In the orientation shown in FIG. 1, the spacing between the bottom surfaces of the two guiding sliding slots 6 located on the left side of FIG. 1 is greater than the spacing between the two guiding sliding slots 6 located on the right side of FIG. 1. With the guiding sliding slots 6 and the bottom surfaces thereof, when the protective cover 2 is turned over to cover the needle hub body 1, the guiding sliding slots 6 are capable of guiding the relative movement direction of the positioning posts 4, so that the positioning posts 4 can slide accurately and quickly and be embedded in the positioning holes 5. For the protective cover 2 and the needle hub body 1, the provision of the guiding sliding slots 6 can simplify the turning over and locking of the protective cover 2 and the needle hub body 1, and ensure that under the premise of a correct turning over direction, even if the strength and angle of the force applied by a user to the protective cover 2 vary every time, the protective cover 2 can still securely cover outside the needle 01.

Reinforcing ribs 7 are provided in a cavity of the protective cover 2 according to the present application. Since the needle hub having a protective cover is formed by an integral injection molding process, the demolding direction of the reinforcing ribs 7 provided in the protective cover 2 is the same as a direction of the lateral opening of the protective cover 2.

In particular, any one of the reinforcing ribs 7 arranged within the cavity of the protective cover 2 is of a planar surface, and the planar surface is perpendicular to the bottom surface of the protective cover 2. Taking FIG. 1 as an example, the bottom surface of the protective cover 2 refers to a face opposite to the direction of the lateral opening of the protective cover 2, and is also referred to as a first curved side wall 21 hereinafter.

For the protective cover 2 according to the present application, the protective cover 2 includes a first curved side wall 21 located at an opposite side of the lateral opening of the protective cover 2. As can be seen, the first curved side wall 21 is the bottom surface as described above. In this example, a finger recess is provided between a root portion and a head portion of the first curved side wall 21. With regard to a usage habit of a user, the shape of the finger recess coincides with the shape of a fingertip of the thumb or index finger of a person, so that it is convenient for the user to apply a pressure to the protective cover 2 through the finger recess to turn over the protective cover 2.

In addition, the protective cover 2 is further provided with a second curved side wall and a third curved side wall, and the two oppositely distributed root side walls referred to above are a part of the second curved side wall and a part of the third curved side wall.

Considering the shape of the protective cover 2 and the needle hub body 1 and the needle 01 to which the protective cover 2 covers, the root portion of the protective cover 2 is smoothly bulged, relative to the head portion of the protective cover 2, whereby the finger recess is formed in a joint surface between the root portion and the head portion of the protective cover 2. Since the root portion of the protective cover 2 is bulged and enlarged compared to the head portion, accordingly, the size of a root portion of the cavity of the protective cover 2 is greater than the size of the head portion of the cavity, which can be better adapted to the shape and dimensions of the needle hub body 1 and the shape and dimensions of the needle 01.

In addition, a plastic joint portion 3, which is integrally injection molded with the needle hub body 1 and the protective cover 2, is provided between the needle hub body 1 and the protective cover 2, and the plastic joint portion 3 is connected to the needle hub body 1 at one end and to the root portion of the protective cover 2 at the other end. When the protective cover 2 is turned over relative to the needle hub body 1, the plastic joint portion 3 is bended and deformed towards the side of the lateral opening of the protective cover 2.

A slender notched groove 8 may be provided on the surface of the plastic joint portion 3. When being turned over, the protective cover 2 is rotated towards the needle hub body 1 and the needle 01 inserted in the needle hub body 1 around a center axis of the notched groove 8.

The notched groove 8 described above has a trapezoidal cross-section, and the width of the notched groove 8 tapers inwardly from the surface of the plastic joint portion 3. Taking FIG. 1 as an example, the cross-section of the notched groove 8 provided on the lower surface of the plastic joint portion 3 is in the shape of an inverted trapezoid with a small top and a large bottom.

A syringe including the needle hub having a protective cover according to any one of the above embodiments is further provided according to the present application.

In addition to the needle hub body 1, the protective cover 2, and the plastic joint portion 3, the syringe may further include a needle barrel 02 having a piston and a push rod, and a needle sheath 03 for covering the needle 01 in an axial direction of the needle 01.

The needle sheath 03 is conventionally configured as a cylindrical needle sheath 03, which is used for the product packaging of the syringe and serves to shield the needle 01, and is usually applied before injection, and needs to be removed and discarded at the time of injection. In contrast, the protective cover 2 according to the present application is used after the injection of the syringe is completed.

The syringe and the needle hub having a protective cover according to the present application are described in detail above. The principle and embodiments of the present application are described through specific examples herein. The description of the above embodiments is merely used to facilitate understanding the method and core idea of the present application. It should be noted that several improvements and modifications can be made to the present application by those skilled in the art without departing from the principles of the present application. These improvements and modifications shall fall within the protection scope of the claims of the present application.

The invention claimed is:

1. A needle hub having a protective cover, wherein the needle hub comprises a needle hub body and the protective cover which are integrally formed by injection molding; the needle hub body is configured for insertion and fixation of a needle; the protective cover is configured to be turned over with an opening thereof facing towards the needle hub body and the needle to cover the needle hub body and the needle; and a root portion of the protective cover is locked to a periphery of the needle hub body when the protective cover is turned over and covers the needle hub body;

wherein a positioning post is provided at the periphery of the needle hub body; and a positioning hole for insertion and positioning of the positioning post is formed in the protective cover;

wherein the number of the positioning post is two and the number of the positioning hole is two, and the two positioning posts are located on two opposite sides of the needle hub body, respectively; the two positioning holes arranged oppositely are provided on a root side wall of the protective cover; and a spacing between the two positioning holes is less than a maximum spacing between the two positioning posts;

wherein the root side wall is further provided with two guiding sliding slots; and a bottom surface of each of the two guiding sliding slots smoothly transitions from an edge of the root side wall to an inner bore rim of each of the two positioning holes.

2. The needle hub having a protective cover according to claim 1, wherein reinforcing ribs are provided in a cavity of the protective cover; and a demolding direction of the reinforcing ribs is the same as a direction of the lateral opening of the protective cover.

3. The needle hub having a protective cover according to claim 1, wherein the protective cover comprises a first curved side wall; the first curved side wall is located at an opposite side of the lateral opening of the protective cover; and a finger recess is provided between a root portion and a head portion of the first curved side wall.

4. The needle hub having a protective cover according to claim 3, wherein the root portion is smoothly bulged, relative to the head portion, to form the finger recess.

5. The needle hub having a protective cover according to claim 1, wherein a plastic joint portion, which is integrally injection molded with the needle hub body and the protective cover, is provided between the needle hub body and the protective cover; a slender notched groove is formed on a surface of the plastic joint portion; and the protective cover is turned over around a center axis of the notched groove and covers the needle hub body and the needle.

6. The needle hub having a protective cover according to claim 5, wherein the notched groove has a trapezoidal cross-section; and a groove width of the notched groove tapers inwardly from the surface of the plastic joint portion.

7. A syringe, comprising the needle hub having a protective cover according to claim 1.

\* \* \* \* \*